United States Patent [19]

Kato

[11] Patent Number: 5,844,019
[45] Date of Patent: Dec. 1, 1998

[54] TOOTH-SURFACE TREATMENT AGENT FOR USE WITH DENTAL GLASS IONOMER CEMENT

[75] Inventor: Shinichi Kato, Tokyo, Japan

[73] Assignee: GC Corporation, Tokyo, Japan

[21] Appl. No.: 948,417

[22] Filed: Oct. 10, 1997

Related U.S. Application Data

[63] Continuation of Ser. No. 593,704, Jan. 29, 1996, abandoned.

[30] Foreign Application Priority Data

Feb. 13, 1995 [JP] Japan ................................. 7-046679

[51] Int. Cl.$^6$ ................................. A61K 6/00; C08K 5/09
[52] U.S. Cl. ........................ 523/116; 523/115; 523/118; 524/178; 524/399; 524/400; 524/435; 524/436; 524/437; 524/556; 524/845
[58] Field of Search .................................. 523/116, 118, 523/115; 524/178, 399, 400, 425, 436, 437, 556, 845

[56] References Cited

U.S. PATENT DOCUMENTS

| | | | |
|---|---|---|---|
| 4,758,612 | 7/1988 | Wilson et al. | 523/116 |
| 4,872,936 | 10/1989 | Engelbrecht | 523/116 |
| 4,952,613 | 8/1990 | Hosoda | 523/109 |
| 5,063,257 | 11/1991 | Akahane et al. | 523/116 |
| 5,065,822 | 11/1991 | Miller et al. | 523/130 |
| 5,094,619 | 3/1992 | McLaughlin | 523/115 |
| 5,374,427 | 12/1994 | Stille et al. | 523/116 |

FOREIGN PATENT DOCUMENTS

| | | | |
|---|---|---|---|
| 2028855 | 3/1980 | United Kingdom | 523/116 |

*Primary Examiner*—Andrew E.C. Merriam
*Attorney, Agent, or Firm*—Oblon, Spivak, McClelland, Maier & Neustadt, P.C.

[57] ABSTRACT

A tooth-surface treatment agent for use with dental glass ionomer cement comprises (a) a polymer of an α-β unsaturated carboxylic acid having a specific molecular weight, (b) a compound containing one or more of the elements selected from the group of aluminum, iron, tin, and calcium, and (c) water. This agent ensures the dissolution and removal of the smear layer, and improves and stabilizes the bonding strength of the glass ionomer cement to tooth structure. Also, the agent has a milder effect than the effects had by phosphoric acid, and has an action on reducing irritation to the dental pulp and is harmless thereto because it enables the smear plugs to remain in dentinal tubules.

6 Claims, No Drawings

TOOTH-SURFACE TREATMENT AGENT FOR USE WITH DENTAL GLASS IONOMER CEMENT

This application is a Continuation of application Ser. No. 08/593,704, filed on Jan. 29, 1996, now abandoned.

BACKGROUND OF THE INVENTION

The present invention relates generally to a tooth-surface treatment agent for use with dental glass ionomer cement. More specifically, this invention is concerned with a tooth-surface treatment agent for use with dental glass ionomer cement, which is clinically used to make the bonding strength or stability of dental glass ionomer cement to tooth structure higher than ones used before.

Dental cement is one of the various dental materials having wide applications. Currently available, representative dental cements include zinc phosphate cement prepared by making use of the reaction of zinc oxide with phosphoric acid, polycarboxylate cement prepared by the reaction of zinc oxide with a polycarboxylic acid, resin cement prepared by the polymerization of an acrylic monomer, and glass ionomer cement prepared by making use of the reaction of fluoroaluminosilicate glass powder with a polycarboxylic acid.

In particular, the glass ionomer cement has numerous advantages, among which:

1. it shows adhesion to tooth structure,
2. it excels in physical properties,
3. it excels in marginal sealing,
4. it is substantially harmless to the dental pulp and excels in bio-affinity,
5. it is semitransparent and in well agreement with tooth structure, and
6. it provides a slow release of fluorine and so is expected to have action on prevention of dental caries and inhibition of the progress of dental caries. For these reasons, the glass ionomer cement has recently found a variety of odontotherapical applications for the restoration and filling of decaying cavities, the attachment of crowns, inlays, bridges, and orthodontic bands, the lining of cavities, core building, and preventive filling.

More recently developed, new types of glass ionomer cement such as a photopolymerized type of glass ionomer cement or a resin hybrid type glass ionomer cement have attracted considerable attention. These types of cement contain an unsaturated organic compound and a polymerization catalyst in addition to fluoroaluminosilicate glass powder and polyacrylic acid that are main components of conventional types of glass ionomer cement, and involve a mechanism which enables that cement to harden due to the photo- or chemical polymerization reaction of the unsaturated organic compound that occurs simultaneously with the neutralization reaction between the fluoroaluminosilicate glass and the polyacrylic acid. This cement substantially eliminates the problems with conventional types of glass ionomer cement such as embrittlement or disintegration and clouding due to contact with moisture at an initial hardening stage, can be handled with ease, and excels in such physical properties as initial hardness, bonding strength to tooth structure, flexural strength, and transparency. With the advance of such new cement in mind, the term "glass ionomer cement" used herein is understood to refer to a type of cement wherein the neutralizing and hardening reaction of fluoroaluminosilicate glass powder (a basic material) with a polycarboxylic acid participates in part, or the whole, of its hardening mechanism.

One major feature of the glass ionomer cement is a chemical adhesion to tooth structure. This adhesion is said to manifest itself through the chelate, hydrogen or ion crosslinking bonding of carboxyl groups in a cement slurry to hydroxyl groups, or metal or hydrogen ions on the surface apatite layer of tooth structure, or organic carboxyl, carbonyl, amino, and imino groups of collagen. This adhesion to tooth structure makes the glass ionomer cement much more superior to conventional types of cement in terms of long-term stability, marginal sealing, decrease of dental pulp irritations, prevention of secondary caries, and other properties, and is said to be one of the greatest advantages achieved by use of the glass ionomer cement.

However, this type of glass ionomer cement has the following problems in connection with bonding to tooth structure.

Dental materials inclusive of glass ionomer cement, which are used for physical and dental bonding to tooth structure, generally do not show the same strength of bonding to each tooth structure, the strength of bonding varying much to different tooth structure; they often fracture or fall off, offering some problems in terms of bonding stability and material retention ratio.

Such unstable bonding strength is primarily caused by the facts that:

1. tooth structure is a living tissue and so varies unavoidably from an individual to another,
2. the bonding of dental materials to tooth structure is inhibited by moisture present in the oral mouth,
3. the bonding of dental material to tooth structure, especially collagen that is the main component of dentin has difficulty, and
4. there is some considerable difference in the bonding strength of dental materials to tooth structure, although depending on how to handle that materials, for instance, when that material is mixed, filled, applied, and cured.

However, the largest cause is, the debris layer, so-called "smear layer" of 1 to 5 $\mu$m in thickness formed by the rubbing of the clinically cut surface of a tooth or the wall of a clinically formed cavity with cuttings, saliva, etc. If this layer is present between the dental material and the wall of a cavity, then the close contact of both is inhibited. As known so far in the art, the smear layer inhibits largely the bonding of dental material to tooth structure, and this is unexceptionally applied to the glass ionomer cement characterized by chemical bonding to tooth structure. Bacteria included in the smear layer are likely to propagate, reportedly resulting in an increased stimulation of discomfort or pain in the dental pulp. To avoid this, too, it is considered to remove the smear layer. Traditional removal of the smear layer has clinically been achieved by etching with phosphoric acid. To this end, phosphoric acid is treated on the surface of a tooth over a constant time, so that the smear layer can be dissolved and cleaned by washing with water. This is primadfacie effective for the treatment of enamel.

However, the phosphoric acid etching has several problems, if it's used for the treatment of dentin. Dentin is a hard tissue constituting the bulk of a tooth has a structure of numberless dentinal tubules running radially from the vicinity of the pulp cavity toward the surface of dentin. Upon dentin cut, a cutting layer is forced into an opening in each dentinal tubule on the cut surface, constituting a so-called "smear plug" structure wherein the opening remains closed as if plugged. The smear layer inhibits the bonding of dental material to teeth as already noted, but this smear plug is considered to have rather beneficial effects; for instance, it reduces the permeation of moisture into the bottom of a cavity, and it cuts off the transmission of external irritation to the dental pulp to have a certain protecting effect on the dental pulp.

However, the use of phosphoric acid ensures removal of the smear layer upon treated therewith because it is a significantly strong acid, but this incurs incidental removal of the smear plug. Consequently, each dentinal tubule is funneled out, resulting in considerable invasions such as considerable decalcification of sound portions of dentin. This, in turn, causes an increased irritation to the dental pulp, and the permeation of moisture into the dentin of the cavity floor to be increased, giving rise to the inhibition of the bonding of dental material to dentin due to the fluids contained in the tubules. The use of such a strong acid also leads to a change in the high-dimensional structure of collagen, which may otherwise results in a lowering of bonding strength.

It is therefore desired to develop a tooth-surface treatment agent for use with dental glass ionomer cement, which enables the smear layer to be dissolved and removed, yet ensures that the bonding strength of the glass ionomer cement to tooth structure is stronger and more stable and ensures that the smear plug remains filled in each tubule because it is milder effect than phosphoric acid.

An object of the present invention is to provide such a tooth-surface treatment agent for use with dental glass ionomer cement.

SUMMARY OF THE INVENTION

According to the present invention, the above-mentioned object is achieved by the provision of a tooth-surface treatment agent for use with dental glass ionomer cement, which comprises (a) a polymer of an $\alpha$-$\beta$ unsaturated carboxylic acid having a weight-average molecular weight of 1,000 to 40,000, (b) a compound containing one or more of the elements selected from the group of aluminum, iron, tin, and calcium, and (c) water. Just before the glass ionomer cement is used, the tooth-surface treatment agent comprising the above (a), (b) and (c) components is treated on tooth surface over a constant period of time, and then washed with water, so that the tooth structure can be washed with removal of the smear layer. This, in turn, ensures that the bonding of the glass ionomer cement to tooth structure can be improved and stabilized. Observation of the thus treated surface under a scanning electron microscope or the like shows that the dentinal tubules remain partially closed, indicating the presence of smear plugs.

In a preferred embodiment of the present invention, the tooth-surface treatment agent for use with dental glass ionomer cement comprises (a) 1 to 80 parts by weight of a polymer of an $\alpha$-$\beta$ unsaturated carboxylic acid having a weight-average molecular weight of 1,000 to 40,000, (b) 0.01 to 30 parts by weight of a compound containing one or more of the elements selected from the group of aluminum, iron, tin, and calcium, and (c) 20 to 100 parts by weight of water. This embodiment is particularly effective when the present invention is carried out.

The tooth-surface treatment agent of the present invention is treated on tooth surface and then washed with water. It is therefore more preferable that the agent is colored so as to make a clear estimation of how treating and water washing take place. Possible use may be made of various coloring materials, among which food dyes are preferred for the present invention, because they are harmless to the human body.

Thus, it is preferable that the tooth-surface treatment agent of the present invention for use with dental glass ionomer cement further includes (d) 0.0001 to 5 parts by weight of a food dye. This ensures that the inventive agent can be used more easily.

Most preferably, the tooth-surface treatment agent of the present invention for use with dental glass ionomer cement further includes (e) 0.1 to 30 parts by weight of a thickener. This enables the inventive agent to have thixotropy in a gelled state and, hence, to be more readily treated on the surface of a tooth.

DETAILED EXPLANATION OF THE INVENTION

The polymer of an $\alpha$-$\beta$ unsaturated carboxylic acid having a weight-average molecular weight of 1,000 to 40,000 used herein is understood to refer to polymers of $\alpha,\beta$-monocarboxylic or dicarboxylic acids, as typically exemplified by homopolymers or copolymers of acrylic acid, methacrylic acid, 2-chloroacrylic acid, aconitic acid, mesaconic acid, maleic acid, itaconic acid, fumaric acid, glutaconic acid, and citraconic acid. The copolymers may be composed of either $\alpha$-$\beta$ unsaturated carboxylic acids or an $\alpha$-$\beta$ unsaturated carboxylic acid and a component copolymerizable therewith. In the latter case, it is preferable that the $\alpha$-$\beta$ unsaturated carboxylic acid accounts for 50% or more of the copolymer. The copolymerizable component used herein, for instance, includes acrylamide, acrylonitrile, methacrylic acid ester, acrylates, vinyl chloride, allyl chloride, and vinyl acetate. Among these polymers of $\alpha$-$\beta$ unsaturated carboxylic acids, particular preference is given to using homopolymers or copolymers of acrylic acid, mathacrylic acid, or maleic acid.

It is not preferable to use an $\alpha$-$\beta$ unsaturated carboxylic acid polymer having a weight-average molecular weight of less than 1,000 because the resulting tooth-surface treatment agent has too low a pH value. In this case, the same problems as is the case with the treatment of the surface of a tooth with phosphoric acid arise such as removal of the smear plugs, and decalcification of sound portions of dentines. When the $\alpha$-$\beta$ unsaturated carboxylic acid polymer used has a weight-average molecular weight exceeding 40,000, the resulting tooth-surface treatment agent is less effective because the pH value becomes too high. Moreover, this agent is likely to cure, resulting in a lowering of its storability. It is therefore essentially required that the $\alpha$-$\beta$ unsaturated carboxylic acid polymer used herein have a weight-average molecular weight of 1,000 to 40,000 inclusive.

Preferably, the tooth-surface treatment agent of the present invention contains 1 to 80 parts by weight of the $\alpha$-$\beta$ unsaturated carboxylic acid polymer. At less than 1 part by weight, the resulting tooth-surface treatment agent for use with glass ionomer cement is less effective whereas at more than 80 parts by weight, the agent have too high a viscosity and so involves some problems during use and storage.

The metal salt contained in the tooth-surface treatment agent of the present invention is believed to aid in the chemical bonding of glass ionomer cement to tooth structure in particular and prevent degeneration of collagen by an acid and contraction of collagen which may occur during water washing and drying. It has now been found that satisfactory bonding strength can be achieved by the addition of one or more of the elements selected from the group consisting of aluminum, iron, tin, and calcium to the tooth-surface treatment agent for use with glass ionomer cement.

The compounds containing one or more of the elements selected from the group consisting of aluminum, iron, tin, and calcium, which are used in the tooth-surface treatment agent of the present invention, for instance, include aluminum chloride, aluminum oxide, aluminum acetate, aluminum salicylate, aluminum acrylate, aluminum oxalate, aluminum hydroxide, aluminum nitrate, aluminum carbonate, aluminum lactate, aluminum fluoride, aluminum sulfate, aluminum itaconate, aluminum phosphate, poly(aluminum) chloride, aluminum iodide, aluminum acetylacetonate, aluminum bromide, aluminum butoxide, aluminum butylate, aluminum ethoxide, aluminum cyclohexanebutyrate, aluminum ethylhexanoate, aluminum isopropoxide, aluminum laurate, aluminum oleate, potassium aluminum sulfate, aluminum stearate, aluminum triethoxide, aluminum triethylate, aluminum triisopropoxide, aluminum triisopropylate, barium aluminate, hydrogenated lithium aluminum, sodium aluminate, iron oxide, iron chloride, iron sulfate, iron nitrate, iron hydroxide, ammonium iron sulfate, iron citrate, iron succinate, iron bromide, iron phosphate, iron dichloride, ethylenediamine iron, iron oxalate, iron lactate, iron ethylenediaminetetraacetate, iron 2-ethylhexanoate, potassium ferrocyanide, potassium ferrycyanide, sodium ferrocyanide acetylacetate, iron alum, sodium iron citrate, sodium iron oxalate, ammonium iron sulfate, iron benzoylacetonate, dicyclopentadienylron, N,N-dimethyl-1-ferrocenylethylamine, decanoic acid iron salt, naphthenic acid iron salt, pentacarbonyliron, nonacarbonyliron, iron perchlorate, phthalocyanineiron, sodium pentacyanonitrosylferrate, sodium pentacyanoammineferrate, dicyanobis(1,10-phenanthroline) iron, tris(1-phenyl-1,3-butandionate)iron, tin oxide, tin chloride, tin acetate, tin phosphate, tin diphosphate, tin pyrophosphate, tin fluoride, tin iodide, tin oxalate, tin sulfate, tin bromide, tin tetrachloride, tin borofluoride, tin 2-ethylhexanoate, triphenyltin hydroxide, bis(tributyltin) oxide, di-n-butyltin diacetate, dibutyltin dichloride, di-n-butyltin dilaurate, dibutyltin oxide, hexabutyltin, bis(2-ethylhexanoic acid) dibutyltin salt, potassium stannate, sodium stannate, tetrabutyltin, tetraethyltin, tetramethyltin, tetraoctyltin, tetraphenyltin, tributyltin acetate, trimethyltin chloride, triethyltin chloride, tripropyltin chloride, tributyltin chloride, calcium acetate, calcium benzoate, calcium chloride, calcium nitrate, calcium nitrite, calcium hydroxide, calcium bromide, calcium carbonate, calcium silicate, calcium oxalate, calcium citrate, calcium phosphate, calcium dihydrogen phosphate, calcium pyrophosphate, phosphorous acid calcium salt, calcium 2-ethylhexanoate, calcium fluoride, calcium formate, calcium gluconate, calcium glycerophosphate, hydrogenated calcium, carcium hypochlorite, calcium iodide, calcium lactate, calcium molybdate, calcium oleate, calcium oxide, cacium palmitate, calcium stearate, calcium D-panthothenate, calcium salicylate, calcium sulfate, calcium sulfide, calcium sulfite, calcium tartarate, calcium tungstate, calcium acrylate, calcium borate, calcium metaborate, calcium propionate, and calcium laurate.

Optionally, these compounds may be used in combination of two or more. It is here to be noted that iron and tin compounds are often present in the form of ferrous and ferric forms and stannous and stannic forms, respectively, all however being available. Hydrous salt forms of the "compound containing one or more of the elements selected from the group consisting of aluminum, iron, tin, and calcium", may be also conveniently used.

In the present invention, it is preferable that the "compound containing, one or more of the elements selected from the group consisting of aluminum, iron, tin, and calcium" is used in a quantitative range of 0.01 to 30 parts by weight. At less than 0.01 part by weight, the metal salts has no good effect on the bonding of the glass ionomer cement to tooth structure. When the quantity of the compounds used exceeds 30 parts by weight, the bonding strength of the glass ionomer cement to tooth structure does not only become worse but the color and storability of the glass ionomer cement get worse as well, because much metal salts remains even after water washing.

In the present invention, the water is an essential component for the dilution of the $\alpha$-$\beta$ unsaturated carboxylic acid polymer, and for the dissolution of the "compound containing or more of the elements selected from the group consisting of aluminum, iron, tin, and calcium". In the present invention, it is preferable that the amount of the water used ranges from 20 parts by weight to 100 parts by weight. At less than 20 parts by weight, the resulting agent has difficulty because it is too high a viscosity, and has a storage problem as well. When the amount of the water used exceeds 100 parts by weight, on the other hand, it becomes difficult for the resulting agent to work as a tooth-surface treatment agent.

In the present invention, both food dyes, natural and synthetic, may be used as the coloring material. However, particular preference is given to using a synthetic food dye because it is a uniform and stable material. Included in the food dyes used for the tooth-surface treatment agent for use with glass ionomer cement, for instance, are synthetic tarry dyes as typically exemplified by food red dye No. 2, food red dye No. 3, food red dye No. 102, food red dye No. 104, food red dye No. 105, food red dye No. 106, food yellow dye No. 4, food yellow dye No. 5, food blue dye No. 1, food blue dye No. 2, food green dye No. 3, and food purple dye No. 1, $\beta$-carotene, iron chlorophyllin sodium, copper chlorophyllin sodium and copper chlorophyll. In some cases, these food dyes may be used in combination of two or more.

In the present invention, the quantity of the food dyes used preferably ranges from 0.0001 part by weight to 5 parts by weight. At less than 0.0001 part by weight, the desired object is not attained because the tooth-surface treatment agent is too thinly colored. When the food dyes is used in excess of 5 parts by weight, on the other hand, tooth structure may possibly remain colored even upon washed with water. The bonding strength of the glass ionomer cement to tooth structure is rather decreased.

In the present invention, it is convenient to use a suitable thickener for the purpose of increasing the viscosity of the agent, thereby imparting thixotropy thereto, because it is used in a gelled state. Any desired thickener, whether organic or inorganic, may be used. Thus, the tooth-surface treatment agents for use with glass ionomer cement, for instance, contain as the thickener anhydrous silica, carboxymethylcellulose calcium, carboxymethyl-cellulose sodium, starch, starch-sodium glycolate, starch-sodium phosphate, methyl cellulose, sodium polyacrylate, alginic acid, sodium alginate, alginic acid-propylene glycol ester, casein, casein sodium, polyethylene glycol, ethyl cellulose, hydroxyethyl cellulose, gum arabic, gluten, locus bean gum, and gelatin. Optionally, these thickener may be used in combination of two or more.

In the present invention, the thickener are preferably used in a quantitative range of 0.1 to 30 parts by weight. At less than 0.1 part by weight, any desired effect on a thickener and thixotropy is not achieved. The use of more than 30 parts by weight of the thickener makes the viscosity of the agent too high for smooth treating, and renders the bonding strength of the glass ionomer cement to tooth structure worse as well.

The present invention will now be explained in further detail with reference to illustrative examples 1–12 directed to the inventive tooth-surface treatment agent for use with dental glass ionomer cement as well as comparative example 1 where no surface treatment agent was used and comparative examples 2–5 directed to a conventional phosphoric acid etching type of tooth-surface treatment agent.

| | |
|---|---|
| Illustrative Example 1 | |
| Polyacrylic acid (with an average molecular weight of 20,000) | 30 parts by weight |
| Aluminum oxalate | 1 part by weight |
| Distilled water | 69 parts by weight |
| Illustrative Example 2 | |
| Polyacrylic acid (with an average molecular weight of 18,000) | 15 parts by weight |
| Distilled water | 77 parts by weight |
| Aluminum chloride | 3 parts by weight |
| Carboxymethylcellulose sodium | 5 parts by weight |
| Food red dye No. 3 | 0.003 parts by weight |
| Illustrative Example 3 | |
| Polyacrylic acid (with an average molecular weight of 22,000) | 20 parts by weight |
| Polymaleic acid (with an average molecular weight of 7,000) | 10 parts by weight |
| Distilled water | 67 parts by weight |
| Ferric chloride | 3 parts by weight |
| Illustrative Example 4 | |
| Polyacrylic acid (with an average molecular weight of 18,000) | 25 parts by weight |
| Polymaleic acid (with an average molecular weight of 9,000) | 15 parts by weight |
| Distilled water | 55 parts by weight |
| Iron citrate | 5 parts by weight |
| Food red dye No. 104 | 0.01 part by weight |
| Illustrative Example 5 | |
| Polyacrylic acid (with an average molecular weight of 25,000) | 10 parts by weight |
| Polyitaconic acid (with an average molecular weight of 8,000) | 10 parts by weight |
| Distilled water | 68 parts by weight |
| Iron oxalate | 4 parts by weight |
| Casein · sodium | 8 parts by weight |
| Food yellow dye No. 4 | 0.005 parts by weight |
| Illustrative Example 6 | |
| Polyacrylic acid (with an average molecular weight of 30,000) | 7 parts by weight |
| Polyglutaconic acid (with an average molecular weight of 10,000) | 13 parts by weight |
| Distilled water | 73 parts by weight |
| Tin oxide | 2 parts by weight |
| Aerogel 380 (a dry silica type of thickener) | 5 parts by weight |
| Food yellow dye No. 5 | 0.03 parts by weight |
| Illustrative Example 7 | |
| Polymethacrylic acid (with an average molecular weight of 10,000) | 30 parts by weight |
| Polymaleic acid (with an average molecular weight of 7,000) | 15 parts by weight |
| Distilled water | 52 parts by weight |
| Tin phosphate | 3 parts by weight |
| Food blue dye No. 1 | 0.005 parts by weight |
| Illustrative Example 8 | |
| Polyacrylic acid (with an average molecular weight of 20,000) | 20 parts by weight |
| Distilled water | 63 parts by weight |
| Calcium chloride | 10 parts by weight |
| Hydroxyethyl cellulose | 7 parts by weight |
| Food blue dye No. 1 | 0.01 part by weight |
| Illustrative Example 9 | |
| Polymethacrylic acid (with an average molecular weight | 20 parts by weight |

-continued

| | |
|---|---|
| of 15,000) | |
| Polyaconitic acid (with an average molecular weight of 7,000) | 10 parts by weight |
| Distilled water | 65 parts by weight |
| Calcium acetate | 5 parts by weight |
| Food green dye No. 3 | 0.003 parts by weight |
| Illustrative Example 10 | |
| | |
| Polyacrylic acid (with an average molecular weight of 25,000) | 30 parts by weight |
| Distilled water | 60 parts by weight |
| Aluminum iodide | 5 parts by weight |
| Calcium oxalate | 5 parts by weight |
| Copper · chlorophyllin · sodium | 0.1 part by weight |
| Illustrative Example 11 | |
| | |
| Acrylic acid-maleic acid copolymer (with an average molecular weight of 18,000 | 20 parts by weight |
| Distilled water | 70 parts by weight |
| Iron succinate | 1 part by weight |
| Aluminum chloride | 1 part by weight |
| Alginic acid-propylene glycol ester | 8 parts by weight |
| Food red dye No. 105 | 0.008 parts by weight |
| Illustrative Example 12 | |
| | |
| Acrylic acid-itaconic acid copolymer (with an average molecular weight of 20,000) | 30 parts by weight |
| Distilled water | 68 parts by weight |
| Tetramethyltin | 2 parts by weight |
| Food blue dye No. 2 | 0.02 parts by weight |
| Comparative Example 1 | |
| | |
| No tooth-surface treatment agent was used. | |
| Comparative Example 2 | |
| | |
| Phosphoric acid | 30 parts by weight |
| Distilled water | 70 parts by weight |
| Food green dye No. 3 | 0.005 parts by weight |
| Comparative Example 3 | |
| | |
| Phosphoric acid | 10 parts by weight |
| Distilled water | 88 parts by weight |
| Aluminum chloride | 2 parts by weight |
| Food red dye No. 2 | 0.01 part by weight |
| Comparative Example 4 | |
| | |
| Phosphoric acid | 5 parts by weight |
| Distilled water | 95 parts by weight |
| Food blue dye No. 1 | 0.005 parts by weight |
| Comparative Example 5 | |
| | |
| Phosphoric acid | 3 parts by weight |
| Distilled water | 90 parts by weight |
| Calcium chloride | 7 parts by weight |
| Food green dye No. 3 | 0.01 part by weight |

Then, the following three dental glass ionomer cements Nos. 1, 2 and 3 were prepared. According to the testing procedures mentioned later, each sample of the glass ionomer cement was bonded to the enamel or dentin of a bovine teeth using the agents according to the illustrative and comparative examples. As already noted, no tooth-surface treatment agent was used in Comparative Example 1.

Conventional Type Dental Glass Ionomer Cement No. 1

Aluminum oxide (23 grams), silicate anhydride (41 grams), strontium fluoride (10 grams), aluminum phosphate (13 grams), and calcium phosphate (13 grams) were sufficiently mixed together, and the mixture was held at a high temperature of 1,100° C. in an electric furnace for 5 hours for glass melting. Following this, the glass melt was cooled, pulverized in a ball mill for 10 hours, and passed through a 200-mesh (ASTM) sieve to obtain cement powders.

Apart from this, polyacrylic acid (45 grams) having an average molecular weight of 20,000 and distilled water (55 grams) were homogenized by a 60-minute stirring and mixing to obtain a cement liquid.

For the purpose of testing, the cement powders (2.5 grams) were mixed with the cement liquid (1.0 gram) for 30 seconds.

Resin Hybrid Type Dental Glass Ionomer Cement No. 2

Aluminum oxide (23 grams), silicate anhydride (41 grams), strontium fluoride (10 grams), aluminum phosphate (13 grams), and calcium phosphate (13 grams) were sufficiently mixed together, and the mixture was held at a high temperature of 1,100° C. in an electric furnace for 5 hours for glass melting. Following this, the glass melt was cooled, pulverized in a ball mill for 10 hours, and passed through a 200-mesh (ASTM) sieve to obtain glass powders. The glass powders (100 grams) with a 10% solution of vinyltriethoxysilane in ethanol (20 grams) were sufficiently mixed in a mortar, and the mixture was then dried at 110° C. for 2 hours in a steam dryer to obtain dried silane powders. The dried silane powders (100 grams) were sufficiently mixed with benzenesulfonyl chloride (1 gram) in a dark room to obtain cement powders.

Apart from this, polyacrylic acid (30 grams) having an average molecular weight of 20,000, di-2-methacryloxyethylhexamethylene dicarbamate (10 grams), neopentyl glycol diacrylate (15 grams), and distilled water (45 grams) were homogenized by a 60-minute stirring and mixing to obtain a cement liquid.

For the purpose of testing, the cement powders (2.5 grams) were mixed with the cement liquid (1.0 gram) for 30 seconds.

Photopolymerized Type Dental Glass Ionomer Cement No. 3

Aluminum oxide (23 grams), silicate anhydride (41 grams), strontium fluoride (10 grams), aluminum phosphate (13 grams), and calcium phosphate (13 grams) were sufficiently mixed together, and the mixture was held at a high temperature of 1,100° C. in an electric furnace for 5 hours for glass melting. Following this, the glass melt was cooled, pulverized in a ball mill for 10 hours, and passed through a 200-mesh (ASTM) sieve to obtain glass powders. The glass powders (100 grams) with a 10% solution of vinyltriethoxysilane in ethanol (20 grams) were sufficiently mixed in a mortar, and the mixture was then dried at 110° C. for 2 hours in a steam dryer to obtain dried silane powders. The dried silane powders (100 grams) were sufficiently mixed with benzenesulfohydroxanmic acid (1 gram), tin fluoride (1 gram) and benzyl dimethyl ketal (1 gram) in a dark room to obtain cement powders.

Apart from this, polyacrylic acid (30 grams) having an average molecular weight of 20,000, di-2-methacryloxyethylhexamethylene dicarbamate (10 grams), neopentyl glycol diacrylate (15 grams), and distilled water (45 grams) were homogenized by a 60-minute stirring and mixing to obtain a cement liquid.

For the purpose of testing, the cement powders (2.5 grams) were mixed with the cement liquid (1.0 gram) for 30 seconds.

Test 1—Test Procedures for Bonding Cements Nos. 1 and 2 to Bovine Teeth

Bovine mandibular incisal teeth with the roots cut out of them were polished upon removal of the dental pulps with the use of the #600 SiC paper to expose the enamel or dentin surfaces. To treat these surfaces, the treatment agents prepared in Illustrative Examples 1–12 and Comparative Examples 2–5 were treated and, after 10 seconds, well washed out using distilled water. Thereafter, the surfaces were dried with air, followed by putting thereon a masking tape having 3-mm diameter holes. Then, Cements Nos. 1 and 2 were placed over the holes. A stainless steel rod was vertically engaged with the holes for cement hardening. Upon the cement hardened, the test pieces were held in a pyrostat maintained at 37° C. and 100% humidity for 24 hours, after which the tensile bonding strengths of the test pieces were found at a crosshead speed of 1 mm/min., using Autograph (made by Shimadzu Corporation). Eight measurements for each test piece were obtained and averaged with a standard deviation. The results are tabulated in Table 1.

Test 2—Test Procedures for Bonding Cement No. 3 to Bovine Teeth

As in Test 1, bovine teeth were polished with SiC paper, and then treated on the thus polished surfaces with the inventive and comparative tooth-surface treatment agents. Thereafter, a masking tape having 3-mm diameter holes with an acrylic ring of 4 mm in inner diameter, 6 mm in outer diameter and 2 mm in height was applied over the enamel dentin surfaces. Subsequently, Cement No. 3 upon mixed was engaged within the acrylic ring, using a celluloid plate, and then irradiated with light for 40 seconds, using a having a tangusten Halogen lamp visible light irradiator "LAXOR" (made by I.C.I., England) for cement hardening. Upon the hardening of cement, the test pieces were held in a pyrostat kept at 37° C. and 100% humidity for 24 hours. Thereafter, the tensile bonding strengths of the test pieces were found at a crosshead speed of 1 mm/min., using Autograph (made by Shimadzu Corporation). Eight measurements for each test pieces were obtained and averaged with a standard deviation. The results are tabulated in Table 1.

Observation of the Smear Layer and the Smear Plugs

Bovine dentine samples were cut out of bovine teeth using a dental diamond bar, and then treated with the tooth-surface treatment agents prepared in Illustrative Examples 1–12 and Comparative Examples 2–5 for 10 seconds, followed by water washing, drying, and using freeze-drying method. The thus prepared test pieces were deposited with gold for observation under a scanning electron microscope.

TABLE 1

| | Tensile Bonding Strength (Kgf/cm$^2$) | | | | | | |
|---|---|---|---|---|---|---|---|
| | Glass ionomer cement No. 1, conventional type | | Glass ionomer cement No. 2, resin hibrid type | | Glass ionomer cement No. 3, photopolymerized type | | Smear |
| | Enamel | Dentine | Enamel | Dentine | Enamel | Dentine | Plugs |
| Example 1 | 72 ± 11 | 55 ± 6 | 108 ± 17 | 92 ± 15 | 115 ± 16 | 99 ± 17 | Found |
| Example 2 | 76 ± 12 | 59 ± 7 | 96 ± 10 | 90 ± 9 | 109 ± 11 | 102 ± 21 | Found |
| Example 3 | 68 ± 8 | 52 ± 5 | 115 ± 21 | 103 ± 18 | 123 ± 17 | 109 ± 20 | Found |
| Example 4 | 78 ± 10 | 65 ± 8 | 118 ± 23 | 108 ± 20 | 117 ± 19 | 103 ± 21 | Found |
| Example 5 | 65 ± 9 | 51 ± 5 | 97 ± 9 | 89 ± 10 | 108 ± 11 | 95 ± 16 | Found |
| Example 6 | 81 ± 12 | 68 ± 10 | 123 ± 26 | 114 ± 20 | 131 ± 21 | 116 ± 25 | Found |

TABLE 1-continued

| | Tensile Bonding Strength (Kgf/cm²) | | | | | | |
|---|---|---|---|---|---|---|---|
| | Glass ionomer cement No. 1, conventional type | | Glass ionomer cement No. 2, resin hibrid type | | Glass ionomer cement No. 3, photopolymerized type | | Smear |
| | Enamel | Dentine | Enamel | Dentine | Enamel | Dentine | Plugs |
| Example 7 | 83 ± 9 | 70 ± 11 | 121 ± 19 | 110 ± 18 | 127 ± 22 | 109 ± 17 | Found |
| Example 8 | 71 ± 9 | 59 ± 9 | 106 ± 12 | 99 ± 13 | 116 ± 19 | 98 ± 16 | Found |
| Example 9 | 78 ± 12 | 63 ± 9 | 110 ± 16 | 97 ± 11 | 122 ± 23 | 103 ± 15 | Found |
| Example 10 | 69 ± 10 | 58 ± 6 | 98 ± 9 | 89 ± 13 | 118 ± 21 | 113 ± 25 | Found |
| Example 11 | 79 ± 12 | 62 ± 7 | 113 ± 21 | 115 ± 23 | 109 ± 15 | 112 ± 23 | Found |
| Example 12 | 72 ± 8 | 60 ± 11 | 116 ± 18 | 109 ± 19 | 130 ± 22 | 121 ± 26 | Found |
| Comparative Example 1 | 42 ± 18 | 31 ± 14(2) | 64 ± 23 | 51 ± 20(1) | 67 ± 25 | 55 ± 23(2) | — |
| Comparative Example 2 | 75 ± 9 | 22 ± 8(3) | 88 ± 10 | 27 ± 9(2) | 82 ± 21 | 26 ± 9(3) | Not found |
| Comparative Example 3 | 79 ± 11 | 29 ± 6(2) | 82 ± 15 | 32 ± 10(3) | 72 ± 23 | 29 ± 9(2) | Not found |
| Comparative Example 4 | 67 ± 8 | 25 ± 6(2) | 87 ± 11 | 35 ± 9(1) | 85 ± 19 | 32 ± 8(3) | Not found |
| Comparative Example 5 | 77 ± 9 | 32 ± 10(2) | 85 ± 19 | 31 ± 9(2) | 78 ± 21 | 31 ± 8(2) | Not found |

The bracketed figures indicate the number of test pieces that came off prior to testing.

The bonding strengths of the three glass ionomer cement samples to tooth structure were more significantly increased in Illustrative Examples 1–12 than in Comparative Example 1 wherein any agent was not used at all. As can be seen from the standard deviations values reported in Table 1, the bonding strengths of the cement samples to tooth structure are less variable, or more stable, in Illustrative Examples 1–12 than in Comparative Example 1 wherein no agent was used at all. Especially in Comparative Example 1 wherein any agent was not treated at all, some of the eight test pieces used in the bonding test to dentin came off prior to tensile strength testing; however, all test pieces were held in place in Illustrative Examples 1–12.

In terms of the bonding strengths of the three glass ionomer cement samples to enamel, Illustrative Examples 1–12 were at least equivalent to Comparative Examples 2–5 wherein the surfaces of teeth were treated with phosphoric acid. In terms of the bonding strengths of the cement samples to dentin, Illustrative Examples 1–12 were much higher than Comparative Examples 2–5. In Comparative Examples 2–5 where the dentin surfaces were treated with phosphoric acid, some test pieces came off prior to testing. Moreover, several examples were lower in the bonding strength to dentin as compared with Comparative Example 1 wherein the test piece was not treated at all. This is probably that dentin were decalcified and degenerated due to some strong acidity of the phosphoric acid used.

Observation of the dentin surfaces of bovine teeth treated with the agents prepared in Illustrative Examples 1–12 under a scanning electron microscope indicates that they are all completely removed on the smear layers, but the dentinal tubules are filled with the smear plugs having action on reducing dental pulp irritations. In Comparative Examples 2–5 wherein the dentin surfaces of bovine teeth were treated with a phosphoric acid etching type of tooth-surface treatment agent, however, they are completely removed on the smear plugs to keep the dentinal tubules completely open, suggesting that considerable dental pulp irritations will be caused.

The inventive tooth-surface treatment agent for use with dental glass ionomer cement ensures that the bonding strength of the glass ionomer cement to tooth structure can be more increased and stabilized than ones used before. In addition, the inventive agent, because of being milder in performance than a phosphoric acid solution, can strip the surfaces of teeth of the smear layers but enables the smear plugs to remain filled in the dentinal tubules, suggesting that dental pulp irritations and damages to dentin can be reduced. Thus, the present invention provides a tooth-surface treatment agent for use with dental glass ionomer cement, which has very excellent, ideal properties.

What is claimed is:

1. A tooth-surface treatment agent for use with dental glass ionomer cement, which comprises:

(a) a polymer of an α,β-unsaturated carboxylic acid having a weight-average molecular weight of 1,000 to 40,000, (b) at least one compound selected from the group consisting of aluminum oxalate, aluminum chloride, aluminum iodide, ferric chloride, iron citrate, iron oxalate, iron succinate, tin oxide, tin phosphate, calcium chloride, calcium acetate, calcium oxalate, and tetramethyl tin, and (c) water such that said treatment agent remains fluid and can be removed by rinsing with additional water prior to using said dental glass ionomer cement.

2. The tooth-surface treatment agent for use with dental glass ionomer cement as recited in claim 1, wherein said polymer of an α-β unsaturated carboxylic acid having a weight-average molecular weight of 1,000 to 40,000 is a copolymer or homopolymer containing one or more of the monomers selected from the group consisting of acrylic acid, methacrylic acid, 2-chloroacrylic acid, 3-chloroacrylic acid, aconitic acid, mesaconic acid, maleic acid, itaconic acid, fumaric acid, glutaconic acid, and citraconic acid.

3. The tooth-surface treatment agent for use with dental glass ionomer cement of claim 1, which further includes (d) a food dye in an amount of 0.0001 to 5 parts by weight.

4. The tooth-surface treatment agent for use with dental glass ionomer cement of claim 1, which further includes (e) a thickener in an amount of 0.1 to 30 parts by weight.

5. The tooth-surface treatment agent of claim 1, wherein said (a) α-β-unsaturated carboxylic acid is present in an amount of 1 to 80 parts by weight; wherein said compound (b) is present in an amount of 0.01 to 30 parts by weight and said (c) is present in an amount of 20 to 100 parts by weight.

6. A method of treating a tooth surface comprising treating a tooth surface with the tooth-surface treatment of claim 1, and removing said tooth-surface treatment by washing with water.

* * * * *